United States Patent
Tezuka et al.

(10) Patent No.: US 8,988,227 B2
(45) Date of Patent: Mar. 24, 2015

(54) ALARM INFORMATION PROCESSING APPARATUS AND ALARM INFORMATION PROCESSING PROGRAM

(75) Inventors: Shinji Tezuka, Tokyo (JP); Hiroko Hagiwara, Tokyo (JP); Masahiro Echigo, Tokyo (JP); Rie Muneshima, Tokyo (JP)

(73) Assignee: Nihon Kohden Corporation (JP)

( * ) Notice: Subject to any disclaimer, the term of this patent is extended or adjusted under 35 U.S.C. 154(b) by 338 days.

(21) Appl. No.: 13/433,695

(22) Filed: Mar. 29, 2012

(65) Prior Publication Data

US 2012/0249332 A1    Oct. 4, 2012

(30) Foreign Application Priority Data

Mar. 29, 2011 (JP) ................. 2011-073059

(51) Int. Cl.
*G08B 23/00* (2006.01)
*G06F 19/00* (2011.01)
*A61B 5/00* (2006.01)
*A61B 5/0205* (2006.01)

(52) U.S. Cl.
CPC ............ *G06F 19/3406* (2013.01); *A61B 5/746* (2013.01); *G06F 19/345* (2013.01); *A61B 5/742* (2013.01); *A61B 5/0205* (2013.01); *A61B 2560/0276* (2013.01)
USPC ....................... 340/573.1; 340/691.6; 600/301

(58) Field of Classification Search
CPC .......................... G06F 19/3406; A61N 1/37247
USPC ........ 340/573.1, 539.12, 691.1, 691.4–691.6; 600/300, 301; 705/3
See application file for complete search history.

(56) References Cited

U.S. PATENT DOCUMENTS

| | | | |
|---|---|---|---|
| 2004/0148193 A1* | 7/2004 | Blackburn | 600/300 |
| 2006/0161054 A1* | 7/2006 | Reuss et al. | 600/300 |
| 2008/0139898 A1 | 6/2008 | Johnson et al. | |
| 2009/0054735 A1 | 2/2009 | Higgins et al. | |
| 2010/0331631 A1* | 12/2010 | MacLaughlin | 600/301 |
| 2011/0202495 A1* | 8/2011 | Gawlick | 340/573.1 |
| 2012/0215075 A1* | 8/2012 | Surace et al. | 600/301 |

FOREIGN PATENT DOCUMENTS

JP    2003-220054    8/2003

OTHER PUBLICATIONS

European Search Report Dated July 27, 2012.
European Patent Office—Office Action Dated May 8, 2013.
"An Integrated Data Management Approach to Manage Health Care Data"—Diogo Guerra, et al.—Jan. 1, 2009.

* cited by examiner

*Primary Examiner* — Thomas Mullen
(74) *Attorney, Agent, or Firm* — Fox Rothschild LLP; Richard C. Woodbridge; Ryan N. Miller (57) ABSTRACT

An information processing apparatus and program having a reading unit configured to read a plurality of alarm information about alarms generated based on abnormalities of biological information of a patient or abnormalities of a medical apparatus, and a control unit configured to associate same alarm contents that are included in the different alarm information in terms of the alarm contents that indicate contents of abnormalities causing the generation of the alarms is provided.

10 Claims, 9 Drawing Sheets

| 40-1 | | 40-2 | 40-3 | 40-4 | 40-5 | 40-6 | 40 | | |
|---|---|---|---|---|---|---|---|---|---|
| 2011/0308 | 10:15 | CIRCULATORY ORGAN WARD | BED-5 | 38 | UPPER LIMIT AND LOWER LIMIT OF ECG | VITAL | ... | ... | ... |
| 2011/03/08 | 10:14 | INTERNAL MEDICAL WARD | BED-3 | - | ARRHYTHMIA | VITAL | | | |
| 2011/03/08 | 09:39 | PEDIATRICS WARD | BED-4 | 77 | UPPER LIMIT AND LOWER LIMIT OF SpO$_2$ | VITAL ←41 | | | |
| 2011/03/07 | 02:48 | CIRCULATORY ORGAN WARD | BED-1 | - | PROBE CHECK | TECHNICAL | ... | ... | ... |
| 2011/03/05 | 22:03 | INTERNAL MEDICAL WARD | BED-2 | 188 | UPPER LIMIT AND LOWER LIMIT OF IBP | VITAL | | | |
| 2011/03/05 | 21:54 | CIRCULATORY ORGAN WARD | BED-3 | 75 | UPPER LIMIT AND LOWER LIMIT OF SpO$_2$ | VITAL ←42 | | | |
| 2011/03/05 | 21:03 | CIRCULATORY ORGAN WARD | BED-3 | 164 | UPPER LIMIT AND LOWER LIMIT OF PR | VITAL | ... | ... | ... |
| 2011/03/05 | 20:38 | CIRCULATORY ORGAN WARD | BED-3 | 57 | UPPER LIMIT AND LOWER LIMIT OF CO$_2$ | VITAL | | | |
| 2011/03/04 | 23:35 | INTERNAL MEDICAL WARD | BED-3 | 33 | UPPER LIMIT AND LOWER LIMIT OF NBP | VITAL | | | |
| 2011/03/04 | 21:05 | CIRCULATORY ORGAN WARD | BED-3 | 57 | UPPER LIMIT AND LOWER LIMIT OF HR | VITAL | | | |

4. EVALUATION RESULT
4.1 ALARM MANAGEMENT INDEX

| ALARM INDEX | ALARM MANAGEMENT INDEX | |
|---|---|---|
| 75 ☺ | 100~80 | GOOD ALARM STATUS |
| | 79~60 | AVERAGE ALARM STATUS |
| | 59~30 | ALARM MANAGEMENT STATUS NECESSARY TO BE IMPROVED |
| | 0~29 | ALARM MANAGEMENT STATUS NECESSARY TO BE URGENTLY IMPROVED |

4.2 AGGREGATION RESULT
*TECHNICAL ALARMS ARE FREQUENTLY GENERATED. (FROM 2.1)
*IN PARTICULAR, ALARMS ASSOCIATED WITH *ECG* AND *SpO2* ARE FREQUENTLY
 GENERATED AND BOTH ALARMS OCCUPY 60% OF WHOLE ALARMS. (FROM 2.2)
*AMONG TECHNICAL ALARMS, THE ALARMS ASSOCIATED WITH *ECG ELECTRODE
 CHECK*, *SpO2 PROBE CHECK*, AND *RADIO WAVE DISCONNECTION* ARE
 FREQUENTLY GENERATED.
 (FROM 2-2) PLEASE SEE 4.3 TREATMENT METHOD FOR TECHNICAL ALARMS.
*ALARMS GENERATED PER HOUR INDICATES THAT THE NUMBER TENDS TO
 INCREASE NEAR 9 O*CLOCK AND 14 O*CLOCK, BUT THERE IS NO REMARKABLE
 HOURLY TENDENCY. (FROM 2-3)
*IN ALARMS GENERATED PER WORK SHIFT, ALARMS DO NOT TEND TO BE
 GENERATED AT A PARTICULAR SHIFT OF WORK. (FROM 2-3)
*IN ALARMS GENERATED PER DAY OF WEEK, ALARMS DO NOT TEND TO BE
 GENERATED AT A PARTICULAR DAY OF WEEK. (FROM 2-3)
*DURING AN AGGREGATION PERIOD, ALARMS ARE GENERATED AT LARGE
 SIGNIFICANTLY IN BED-5. ALARMS OF SPECIFIC BED IS CAUSING THE TOTAL
 NUMBER OF ALARMS IN ALL FACILITIES TO INCREASE. (FROM 2-4) PLEASE SEE4-3
 TREATMENT METHOD.
DURATION OF TECHNICAL ALARMS IS LENGTHENED. (FROM 2-5) PLEASE SEE 4-3
 TREATMENT METHOD 4-3. TREATMENT METHOD
*TREATMENT FOR ELECTRODE CHECK
PLEASE TRY TO EXCHANGE ELECTRODE AT LEAST ONCE PER DAY
WITH ELECTRODE, BETWEEN ELECTRODE AND SKIN BY DRYNESS
OF ELECTRODE ...
FOR PATIENTS WHO ARE PRONE TO CONSIDERABLE BODY MOVEMENT, ...
*TREATMENT FOR PROBE CHECK
 SpO2 PROBE IS ...
*TREATMENT FOR RADIO WAVE DISCONNECTION
*TREATMENT FOR RADIO WAVE DISCONNECTION IS

ALARM INFORMATION PROCESSING APPARATUS AND ALARM INFORMATION PROCESSING PROGRAM

CROSS-REFERENCE TO RELATED APPLICATION

This application is based on Japanese Patent Application No. 2011-073059 filed on Mar. 29, 2011, the contents of which are incorporated herein by reference.

BACKGROUND

1. Technical Field

Provided is an information processing apparatus and an information processing program.

2. Description of Related Art

In a medical environment, medical apparatuses that generate alarms to detect abnormalities are used. The alarms are generated when abnormalities of health conditions of patients or abnormalities associated with parts of the medical apparatuses are detected. By medical staffs treating patients according to the alarms, the life and health of the patients are expected to be maintained.

These alarms are generally stored as an alarm history. By storing the alarm history, medical staffs not only can deal with emerging abnormalities, but also can accurately comprehend the patients' conditions later if the medical staffs must be away from the patients.

There has been a technique of storing the contents of abnormalities causing the alarms (hereafter, referred to as alarm contents) in the order of the generation of the alarms as an alarm history (log), which his displayed in a list form (for example, Japanese Patent Publication No. H09-131324). Because a given abnormality and the generation time of such abnormality are displayed as a list, the time when the abnormality has occurred can be clearly seen.

See Japanese Patent Publication No. H09-131324.

However, in the art disclosed in the above Japanese Patent Publication, the alarm contents are associated with the generation time thereof and are merely chronologically listed. Since the alarm contents generated at different times are not associated with each other at all, they are useless to comprehend at glance the relevance between the alarm contents. Thus, with such art, one cannot study the recurring condition or rules considering the occurrence situations of the alarms generated in the past. In other words, the obtained data with effort are not statistically processed.

The present invention has been made in the light of the above-mentioned problem. An object of the present invention is to provide an information processing apparatus and an information processing program to associate alarm contents with each other stored in an alarm history.

SUMMARY

To achieve at least one of the above-mentioned objects, an information processing apparatus reflecting one aspect of the present invention comprises a reading unit and a control unit. The reading unit is configured to read a plurality of alarm information related to alarms generated based on abnormalities of biological information of a patient or abnormalities of a medical apparatus. The control unit is configured to associate alarm contents each other, which are included in the alarm information and indicate contents of abnormalities causing the generation of the alarms, with the same alarm contents included in other alarm information.

The objects, features, and characteristics of this invention other than those set forth above will become apparent from the description given herein below with reference to preferred embodiments illustrated in the accompanying drawings.

DETAILED DESCRIPTION

The embodiments of this invention will be described below with reference to the accompanying drawings.

Figure 1:
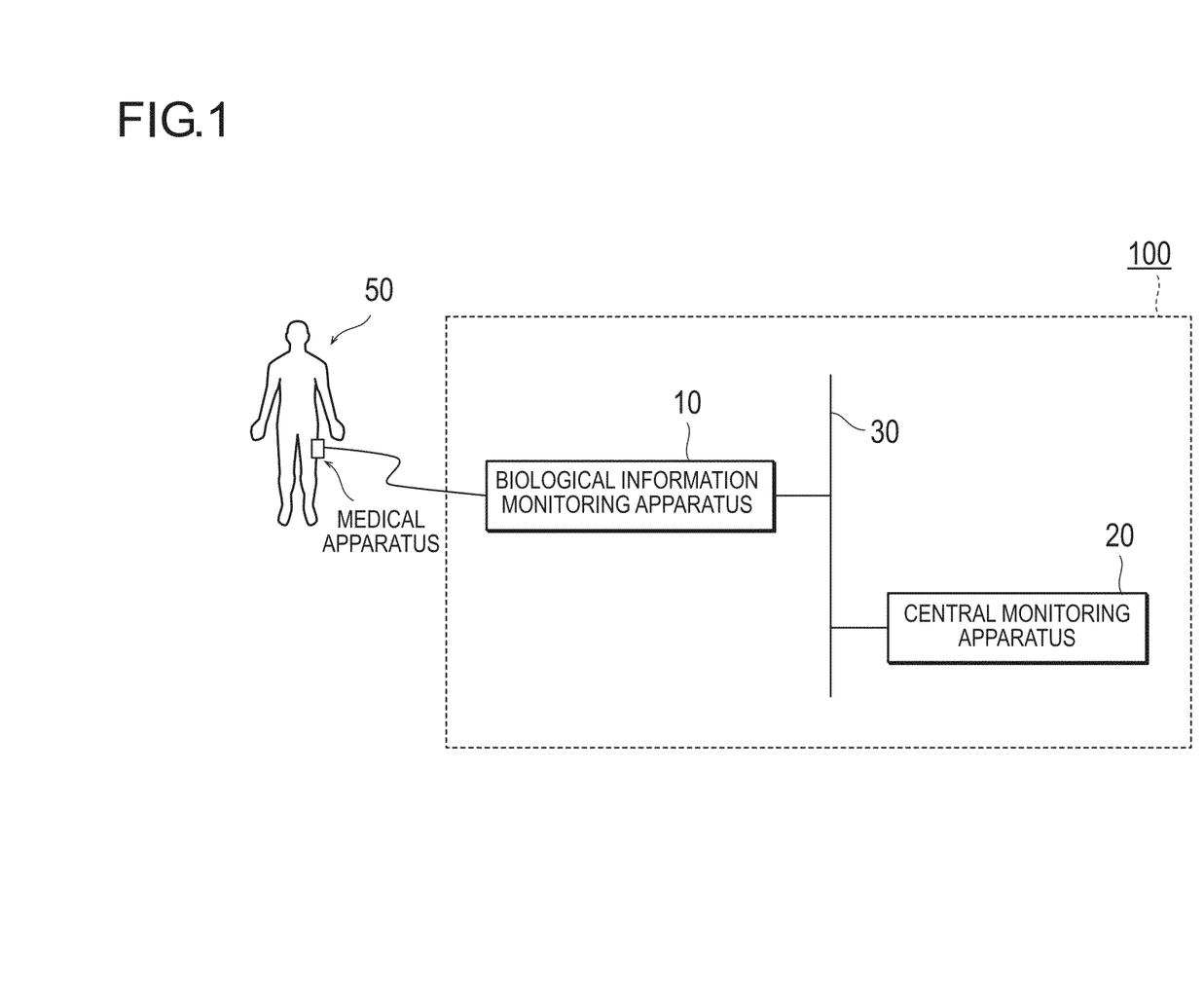
FIG. 1 is a block diagram illustrating the entire configuration of a biological information monitoring system according to an embodiment.
Figure 2:
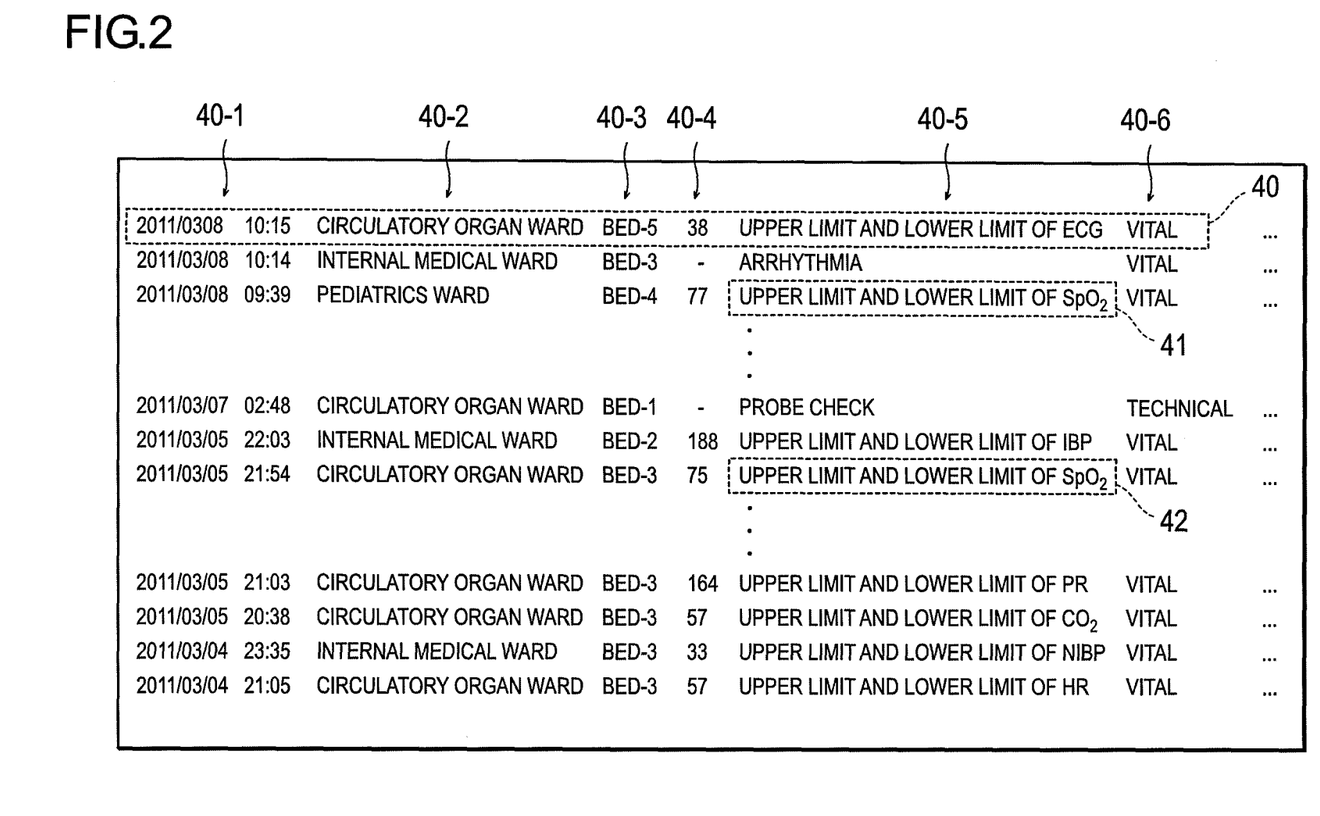
FIG. 2 is a diagram illustrating an example of alarm information and alarm contents.

FIG. 1 is a block diagram illustrating the entire configuration of a biological information monitoring system according to an embodiment. FIG. 2 is a diagram illustrating an example of alarm information and alarm contents.

A biological information monitoring system 100 is provided which includes a biological information monitoring apparatus 10, a central monitoring apparatus 20, and a network 30. Also, a sensor such as a probe to obtain biological information is provided to a patient 50 and is connected to the biological information monitoring apparatus 10.

The biological information monitoring apparatus 10, which could be a monitor or the like placed at a patient's bedside, measures various kinds of biological information. The biological information measured by the biological information monitoring apparatus 10 includes electrocardiogram (ECG), arterial oxygen saturation ($SpO_2$), invasive blood pressure (IBP), non-invasive blood pressure (NIBP), respiration (RESP), and an amount of carbon dioxide ($CO_2$) contained in the exhaled and inhaled air. For example, the biological information monitoring apparatus 10 measuring ECG detects an abnormality regarding the upper limit and the lower limit of an arrhythmia or a heart rate (HR) as a vital alarm indicating a biological abnormality. Also, the biological information monitoring apparatus 10 detects a technical abnormality of the apparatus as a technical alarm, for example, when there is an intrinsic noise present in a measured signal or when there is no signal generated from one or more electrodes. Meanwhile, the biological information monitoring apparatus 10 measuring $SpO_2$ detects an abnormality regarding the upper limit and the lower limit of $SpO_2$ or a pulse rate (PR) as a vital alarm. Also, when a signal or a pulse wave is not received normally from the probe, the biological information monitoring apparatus 10 detects the abnormality regarding the signal or the pulse wave as a technical alarm. Such biological information measurement can be performed invasively or non-invasively.

Upon detection of an abnormality, the biological information monitoring apparatus 10 generates an alarm. Simultaneously, information related to the abnormality causing the generation of the alarm is stored as alarm information in the biological information monitoring apparatus 10. An example of the stored alarm information is illustrated in FIG. 2. As illustrated in FIG. 2, the alarm information 40 includes a plurality of alarm contents 40-1 to 40-6 and is arranged as well as stored in a chronological order in a line form. The alarm content 40-1 indicates a time at which an alarm was generated. The time can be stored up to the second unit scale. The alarm content 40-2 indicates a place where an alarm was generated. As illustrated in FIG. 2, the alarm information can be obtained from different biological information monitoring apparatuses 10 at different places. The alarm content 40-3 indicates a bed identification number of a patient from who an alarm was generated. Alternatively, the bed identification number could be identification information of a patient (for example, the name of a patient).

The alarm content 40-4 indicates a measurement value of the biological information measured by the biological information monitoring apparatus 10. The alarm content 40-5 indicates the contents of an alarm corresponding to an abnormality of the biological information detected by the biological information monitoring apparatus 10. For example, with regard to ECG as a parameter, the information of "arrhythmia" or "the upper limit and the lower limit of a heart rate (HR)" etc. is included as the alarm contents. Also, with regard to SpO2, the information of "the upper limit and the lower limit of SpO2" or "the upper limit and the lower limit of PR" etc. is included as the alarm contents. Further, with regard to IBP, NIBP, RESP, and CO2, the information of the upper limit and the lower limit of each parameter is included in the alarm contents. The alarm content 40-6 indicates whether a generated alarm is an alarm associated with an abnormality in biological information or an alarm associated with a technical abnormality, and indicates whether the generated alarm is the above-described vital alarm or the above-described technical alarm. Further, the alarm contents include "analysis disabled" and "electrode check" as a technical alarm with regard to ECG and include "probe check", "pulse wave detection disabled", and "extrinsic light noise" as a technical alarm with regard to SpO2. Also, among the technical alarms, the contents such as "radio wave disconnection" etc. may be included as an alarm content which is not associated with any other parameters. Alternatively, the alarm information may include information related to duration of time during which an alarm is generated and then stopped or information related to contents indicating if a treatment corresponding to the alarm information is performed by medical staffs.

The central monitoring apparatus 20 obtains the alarm information from one or more biological information monitoring apparatuses 10 connected to the network 30. The central monitoring apparatus 20 performs a managing process such as monitoring the status of the biological information monitoring apparatuses 10. Also, the central monitoring apparatus 20 can be configured to obtain biological information itself and perform the alarm information processing while performing the managing process. A program used to process the alarm information according to the present embodiment is installed in the central monitoring apparatus 20 so as to perform a process of associating the alarm contents. The sequence of the process of associating the alarm content will be described later.

The network 30 is constituted from a local area network (LAN) in which computers or networks are connected to each other in conformity to a standard such as Ethernet®, a token ring, or an FDDI or a wide area network (WAN) in which LANs are connected to each other by dedicated lines. Here, the kind of apparatus or the number of apparatuses connected to the network 30 is not limited to the example illustrated in FIG. 1. For example, the network 30 may have a connection to a printer that prints the processed result by the central monitoring apparatus 20, or a personal computer (PC) or a portable terminal that displays the processed result.

Alternatively, the biological information may be transmitted to the central monitoring apparatus 20, and the central monitoring apparatus 20 may as well have the equivalent functions of the biological information monitoring apparatus 10.

Figure 3:
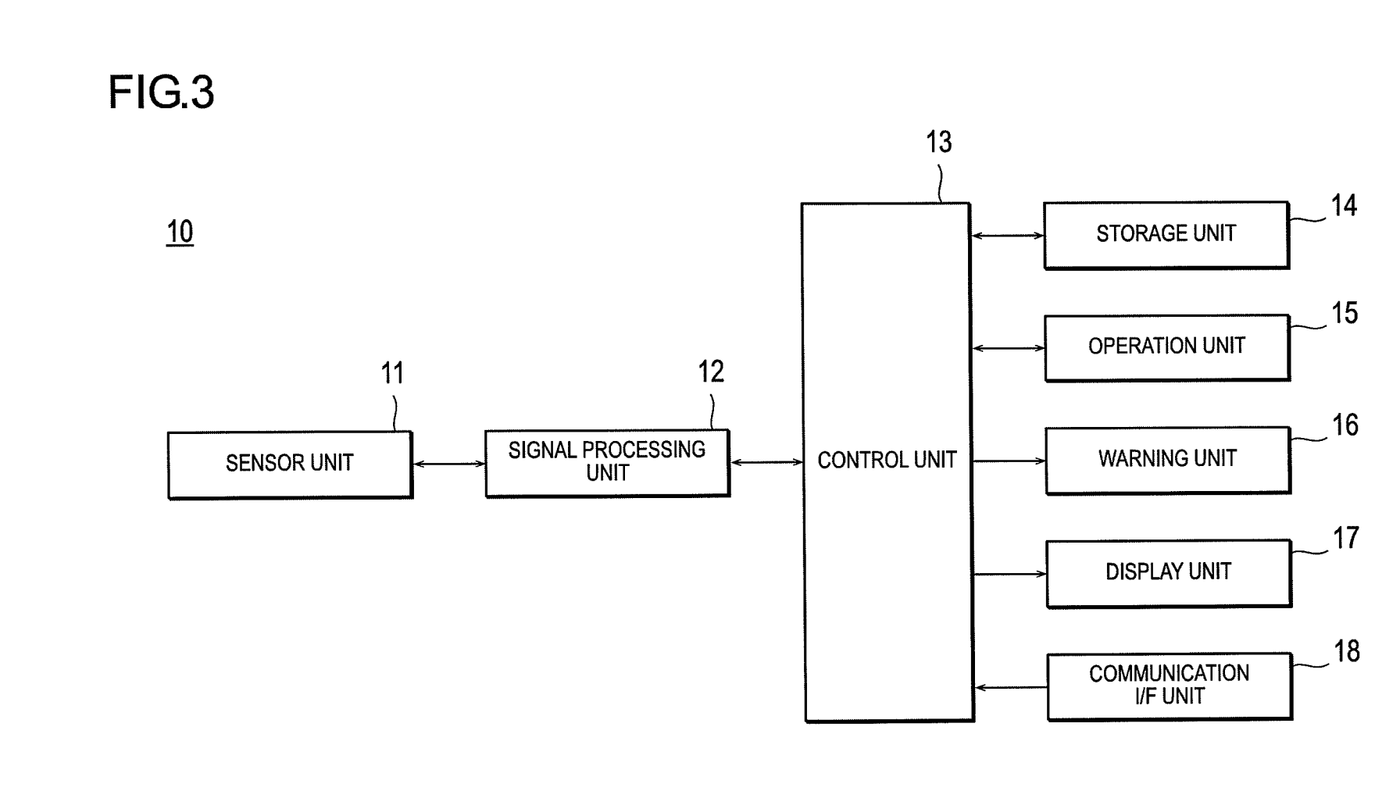
FIG. 3 is a block diagram illustrating the configuration of a biological information monitoring apparatus according to an embodiment.

FIG. 3 is a block diagram illustrating the configuration of the biological information monitoring apparatus 10 according to an embodiment. The biological information monitoring apparatus 10 according to this embodiment comprises a sensor unit 11, a signal processing unit 12, a control unit 13, a storage unit 14, an operation unit 15, a warning unit 16, a display unit 17, and a communication I/F (interface) unit 18. These units are connected to each other through a bus, a cable, or the like to transmit and receive signals each other.

The sensor unit 11 is mounted on the living body of a patient and obtains the biological information from the living body. For example, the sensor unit 11 may be an electrode pad, a catheter including a transducer, a cuff, a probe, or an optical sensor portion of a capnometer. The biological information obtained by the sensor unit 11 is transmitted, for example as an analog signal, to the signal processing unit 12.

The signal processing unit 12 receives the biological information obtained by the sensor unit 11 and processes the biological information. For example, the signal processing unit 12 performs signal amplification, FFT (Fast Fourier Transform), A/D conversion, or the like and converts the biological information into a biological signal interpretable by the control unit 13. The biological signal processed by the signal processing unit 12 is transmitted to the control unit 13. Alternatively, the biological information may be transmitted to the control unit 13 without passing through the signal processing unit 12 and received as a biological signal.

The control unit 13 comprises a CPU (central processing unit), a ROM (read only memory), and a RAM (random access memory) (all of which are not illustrated). These constituent elements are connected to each other through an internal bus of the control unit 13. The CPU controls each unit and executes various arithmetic processes in accordance with programs. The ROM or the RAM stores various programs or various kinds of data. Each function of the control unit 13 is actualized by the CPU's executing a program corresponding to each function. For example, the control unit 13 determines whether the biological information reaches a threshold value or not. When the control unit 13 determines that the biological information reached the threshold value, the control unit 13 detects an abnormality and generates an alarm. Simultaneously, the control unit 13 generates alarm information corresponding to the alarm causing generation of the abnormality. The alarm information, as described in FIG. 2, includes a plurality of alarm contents and is stored as a log in the storage unit 14 etc. Also, the control unit 13 executes a process of associating the same alarm contents with each other to aggregate the number of times that same alarm contents generated and produces data for display such as a graph based on the result obtained by the aggregation. Further, the control unit 13 can read the plurality of alarm contents regarding time and calculate the duration of time during which an alarm has been generated and stopped.

The storage unit 14 is constituted from a flash memory, an HDD (hard disk drive) etc. and stores various programs, including an operation system, to control each constituent element of the biological information monitoring apparatus 10. Also, the storage unit 14 stores parameters associated with the biological information and the threshold value of each parameter. The storage unit 14 stores a program that compares the threshold value to the biological information obtained by the sensor unit 11 and determines whether the biological information reached the threshold value. Also, the storage unit 14 stores a program, that associates the alarm contents in the alarm information with each other and counts the number of alarms generated, and stores data regarding a message used to display the evaluation result based on the number of alarms generated. Also, the storage unit 14 stores a program that counts the time during which an alarm is generated and stopped. Also, the storage unit 14 stores data regarding alarm generation status in all the associated areas.

The operation unit 15 receives various kinds of settings from a user. For example, the operation unit 15 receives a setting about a threshold value of the biological information from medical staff in charge of a patient. Also, the operation unit 15 receives from the user a setting about a period during which a statistical process is performed with regard to the alarm information, a setting about the form of a graph used to display the kinds of biological information, or the result of the processed biological information.

The warning unit 16 issues a warning based on the determination by the control unit 13. Specifically, when the biological signal is determined to have reached a threshold value by the control unit 13, an instruction to issue a warning is delivered from the control unit 13 to the warning unit 16. And the warning unit 16 issues the warning. Here, the warning unit 16 may issue a warning as an auditory or visual alarm.

The display unit 17 is a display such as an LCD (liquid crystal display) or an OLED (organic light emitting display) and displays various kinds of information. For example, the display unit 17 can display a measured value and a threshold value based on image data regarding the measured value of the biological information generated and transmitted by the control unit 13. For example, the measured value and the threshold value are displayed in the form of a polygonal line graph. The display unit 17 can display the statistically processed result of the alarm information aggregated or summarized by the control unit 13. Here, the display unit 17 can be configured as a touch panel as being unified with the operation unit 15. In addition, the display unit 17 can display a warning of the warning unit 16.

The display unit 17 can also be provided with a printer and suitably display various kinds of information indicated on the display apparatus in a printed form as necessary.

The communication I/F unit 18 is a network interface or a serial interface in conformity to a standard such as Ethernet®, a token ring, or an FDDI (fiber-distributed data interface). The communication I/F unit 18 receives an input signal from an external apparatus and transmits the received signal to the control unit 13. The external apparatus includes, for example, a medical apparatus or a PC that obtains a different kind of biological information from the biological information obtained by the biological information monitoring apparatus 10.

Meanwhile, the central monitoring apparatus 20 can comprise substantially the same configuration as the biological information monitoring apparatus 10. Also, the central monitoring apparatus 20 obtains the alarm information generated by the central monitoring apparatus 20 itself as well as the alarm information obtained from the biological information monitoring apparatus 10 through the network 30. Also, when managing the biological information monitoring apparatus 10 in accordance with, for example, an SNMP (simple network management protocol), the central monitoring apparatus 20 is stored with an application to function as an SNMP manager. In this case, an application to function as an SNMP agent is stored in the biological information monitoring apparatus 10.

Further, the biological information monitoring apparatus 10 and the central monitoring apparatus 20 may be configured to communicate with each other in accordance with a protocol such as IHE (Integrating the Healthcare Enterprise), HL 7 (Health Level Seven), DICOM (Digital Imaging and COmmunication in Medicine) or SOAP (Simple Object Access Protocol). Also, the biological information monitoring apparatus 10 and the central monitoring apparatus 20 may include constituent elements other than ones mentioned above or may not include some of the constituent elements mentioned above.

Process of Associating as well as Aggregating and Evaluating Alarm Contents

Next, referring to FIG. 4, a process will be described; wherein the central monitoring apparatus obtains alarm information from the biological information monitoring apparatus, reads the alarm information, associates the alarm contents each other, and displays the evaluation of the aggregation result of the association.

Figure 4:
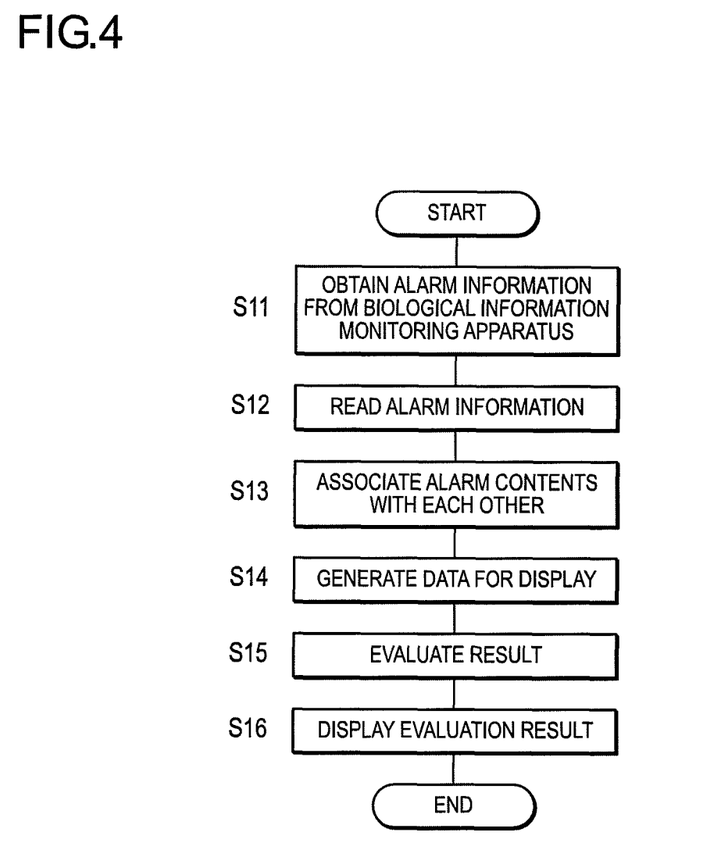
FIG. 4 is a flowchart illustrating the sequence of a process for obtaining the alarm information, associating and evaluating the alarm contents, and displaying the result.

FIG. 4 is a flowchart illustrating a sequence of a process for obtaining the alarm information, associating as well as evaluating the alarm contents, and displaying its result. As illustrated in FIG. 4, the central monitoring apparatus first obtains the alarm information from the biological information monitoring apparatus (Step S11). In this step, information related to the alarms stored in the biological information monitoring apparatus 10 is obtained by the central monitoring apparatus 20. The obtained alarm information is suitably stored in the storage unit.

Next, the stored alarm information is read (Step S12). In this step, the alarm information obtained and stored in Step S11 is read by the control unit.

Next, association in terms of the alarm contents is performed (Step S13). In this step, a process of associating the alarm contents included in the alarm information read in Step S12 is performed. For example, as illustrated in the information 41 and the information 42 of FIG. 2, since the alarm information in different two lines of information includes the common alarm contents "the upper limit and the lower limit of SpO2," the number of generations of the alarm including that alarm content is aggregated. In this case, since the number of pieces of the alarm information including "the upper limit and the lower limit of SpO2" is two, "2" is calculated as the aggregation result. In terms of the other alarm contents, the number of alarm generation incidences can be aggregated in the same manner. Here, the number of alarm generation incidences can be aggregated in terms of a period. An arbitrary period such as "2011/3/4 to 2011/3/7" can be designated at the operation unit 15 or the like.

Next, data for display is produced (Step S14). In this step, the data for display is produced based on the result aggregated in Step S13. The data for display includes numerals, figures, tables, graphs, colors, and characters and are the data to be displayed or the data to be printed out. Specifically, the data for display is produced in the form in which users easily understand the generation status of the alarms generated in the past. Examples of the data for display are described later with reference to FIGS. 5 to 8.

Next, the aggregation result is evaluated (Step S15). In this step, the aggregation result is evaluated based on the data produced in Step S14. Specifically, in addition to producing the data for display, the generation status of the alarms generated in the past as well as the treatment for the alarms etc. are evaluated. Such evaluation can be displayed, for example, by allowing a message prepared in advance based on the data produced in Step S14 to correspond to data value. Examples of the evaluation will be described later with reference to FIG. 9.

Next, the examples of data display indicating the alarm generation status and the evaluation result according to an embodiment will be described with reference to FIGS. 5 to 9.

Figure 5:
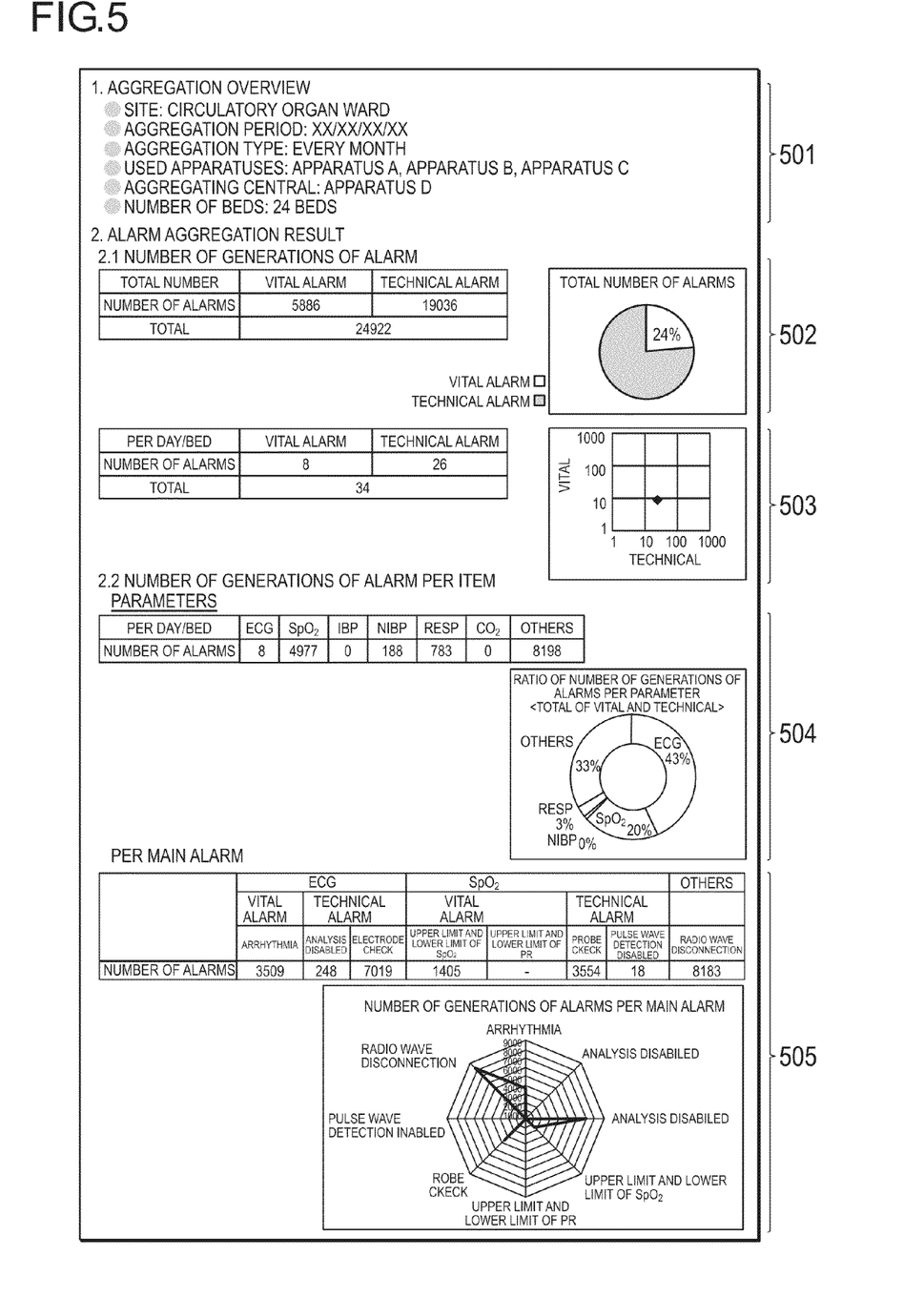
FIG. 5 is a diagram illustrating an example of data for display according to an embodiment.

FIG. 5 is a diagram illustrating an example of display data according to the present embodiment. As illustrated in FIG. 5, data regarding the number of the generated alarms is expressed in an easily understandable form at a glance in the present embodiment. Specifically, tables and graphs are generated to express the number of generation incidences of the alarms indicated by the alarm information included in the log. Section 501 indicates character information that represents the overview of the whole data for display in terms of such as a place, a date, a period—about which data are aggregated—as well as an apparatus used to aggregate the data, etc. Also, a table of Section 502 indicates data regarding the number of the generated alarms aggregated for each of the alarm contents of a vital alarm or a technical alarm. Also, the circle graph of Section 502 visually expresses the ratios of the number of the vital alarms generated to that of the technical alarm. A table of Section 503 indicates the average number of the generated alarms for each bed per day. Also, the logarithmic graph of Section 503 shows the average number generated alarms, in which the vital alarms are compared to those of technical alarms. Also, a table of Section 504 indicates an aggregate number of the generated alarms in terms of parameters. The number of the generated alarms for each parameter can be illustrated by a circle graph of Section 504 so as to illustrate which abnormalities of a given parameter is frequently generated. Also, the table of Section 505 illustrates the total number of each generated alarm including the detailed contents, in that the alarm contents are classified into the vital alarms and the technical alarms in accordance with the respective parameters, each of which is further classified into the detailed contents. The aggregation result can be expressed by a radar chart illustrated in Section 505 so as to enable one to easily understand at a glance the numbers of the generated alarms with the respective detailed contents.

Figure 6:
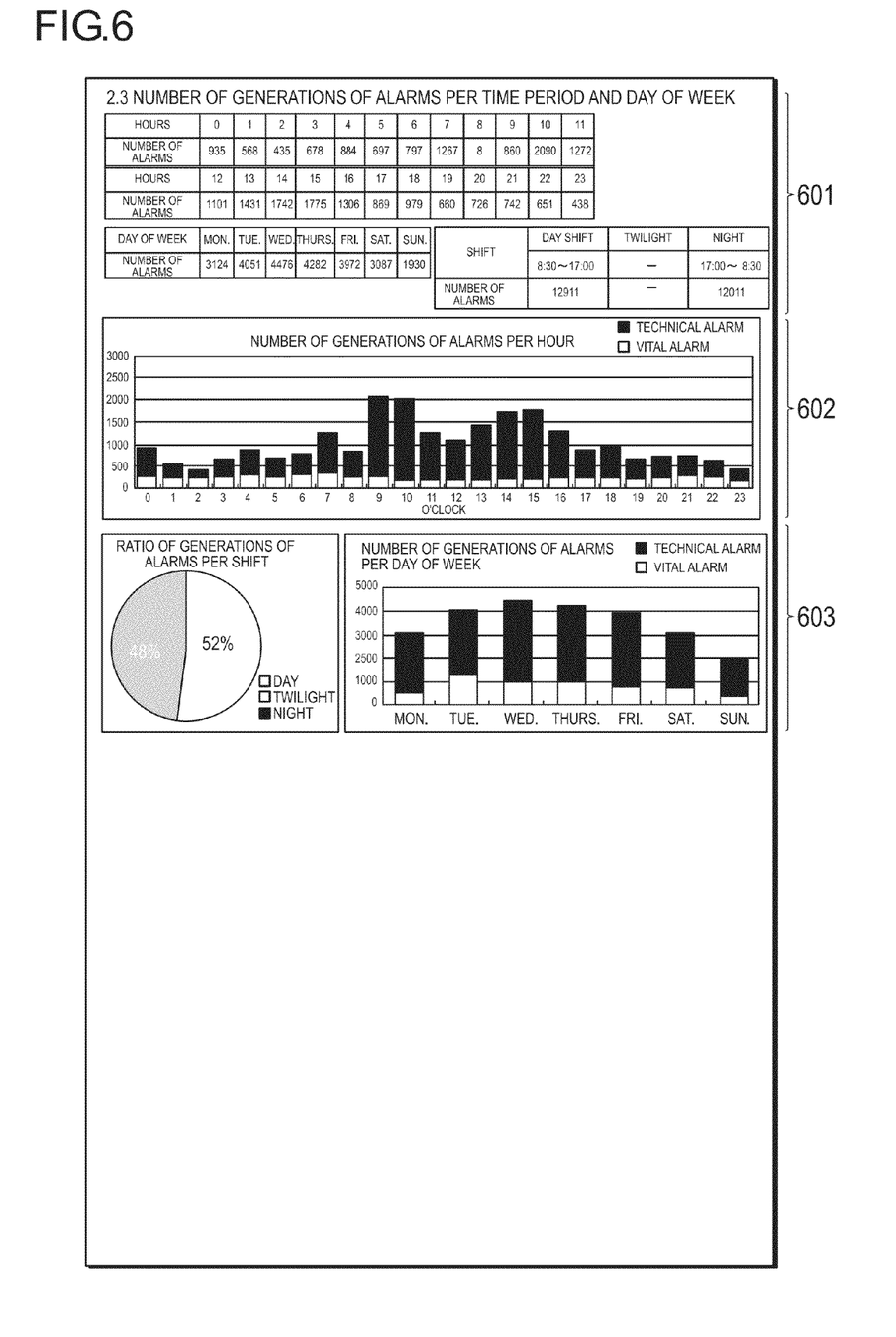
FIG. 6 is a diagram illustrating another example of data for display according to an embodiment.

FIG. 6 is a diagram illustrating another example of display data. In an embodiment, as illustrated in Section 601 of FIG. 6, the number of generations of the alarms is aggregated in terms of time of a desired day, day of a desired week, or shift of a desired day. A bar graph of Section 602 illustrates the total numbers of generations of the vital alarms and the technical alarms in terms of hours, wherein each bar indicating the vital or technical alarms is painted in different colors. Also in Section 603, the numbers of generations of the alarms per shift or per day of the week are illustrated by a circle graph and a bar graph.

Figure 7:
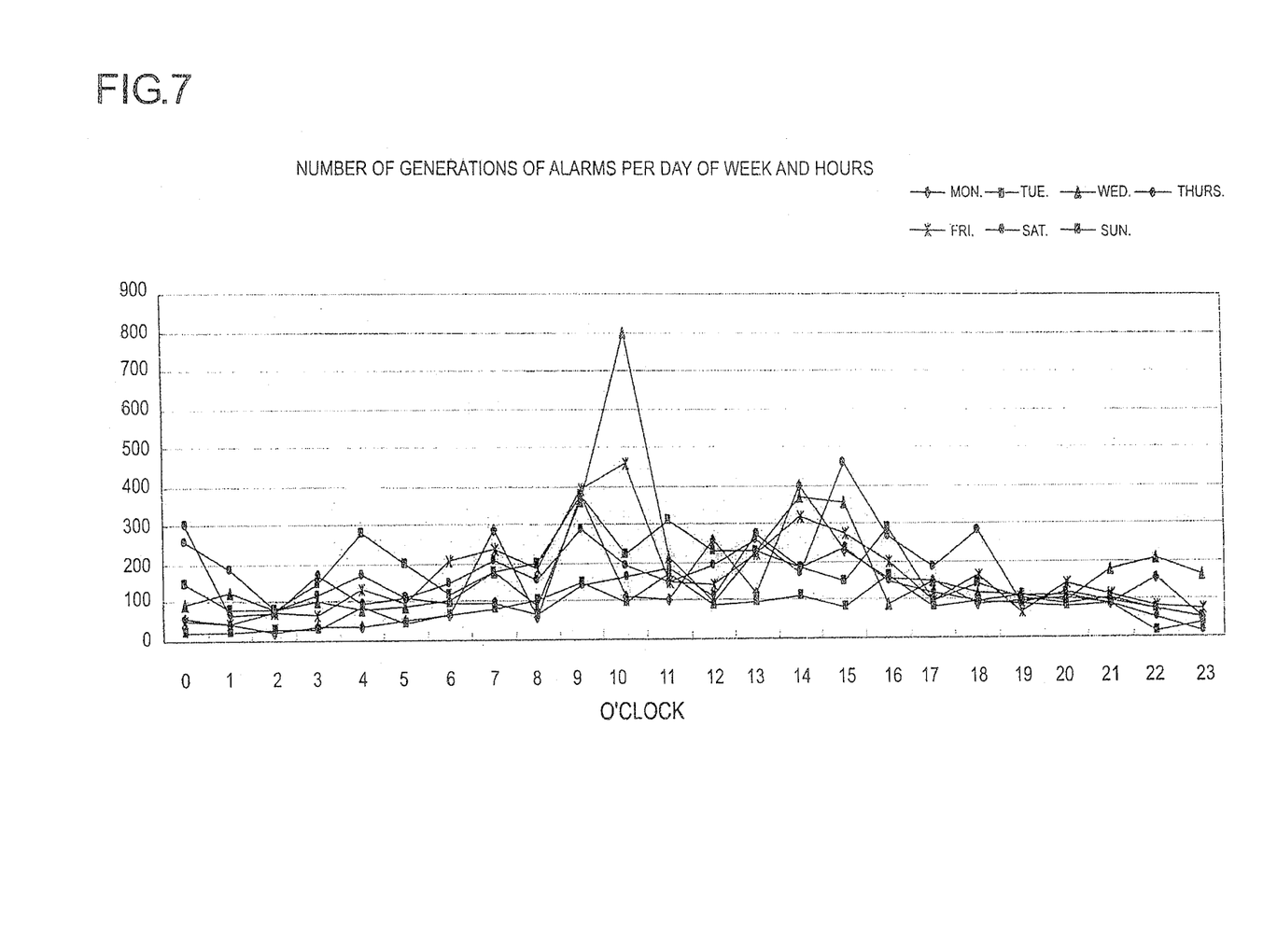
FIG. 7 is a diagram illustrating another example of data for display according to an embodiment.

FIG. 7 is a diagram illustrating another example of data for display according to the present embodiment. In the present embodiment, as illustrated in FIG. 7, the numbers of generations of the alarms in terms of the hours and the days of the week are illustrated together with one polygonal line to enable them to be easily understood at a glance by displaying the numbers of hourly generations of the alarms in in terms of the days of the week.

Figure 8:
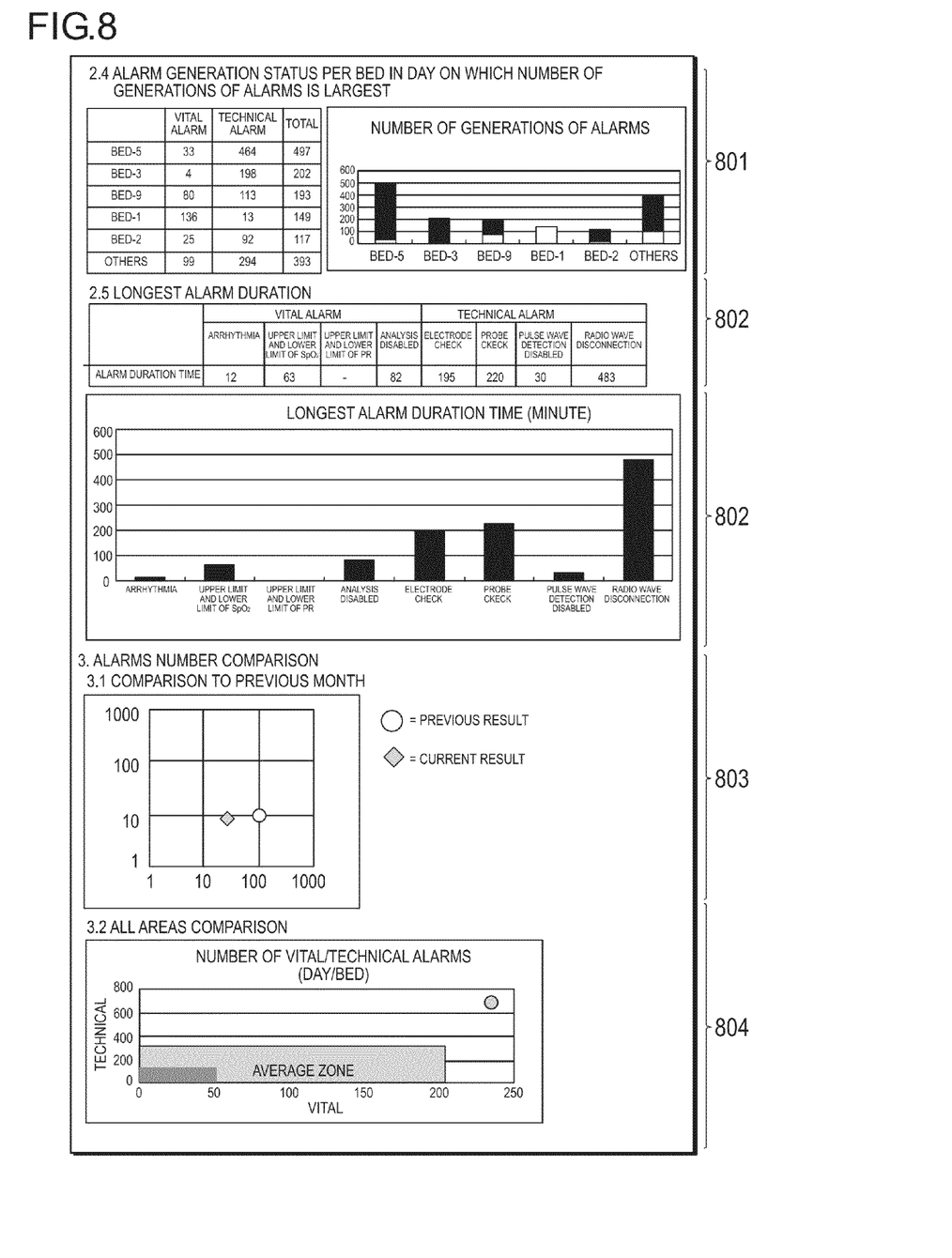
FIG. 8 is a diagram illustrating another example of data for display according to an embodiment.

FIG. 8 is a diagram illustrating another example of data for display according to the present embodiment. As illustrated in Section 801 of FIG. 8, the number of the vital and technical alarms generated in terms of the beds are illustrated about the day on which the number of the generated alarms are largest. And, these data are displayed by a bar graph. Also, as illustrated in Section 802, the duration of time from when an alarm is generated to when the alarm is stopped is illustrated, wherein the alarm has the longest duration of time from when the alarm is generated to when the alarm is stopped. The number of the alarms generated is aggregated for each parameter and is summarized and output based on the aggregation into the bar graph. Here, as illustrated in the table in Section 802, the duration of time from when the alarm is generated to when the alarm is stopped is aggregated by associating the vital alarms and the technical alarms. And, the data for display are produced. Also, in the present embodiment, the total numbers of the alarms generated per month is compared to the total numbers of the alarms generated in the previous month. The comparison result is displayed by a logarithmic graph as illustrated in Section 803. Also, as illustrated in Section 804, the technical alarms are compared to the vital alarms. And, the comparison result may preferably be graphed together with the data such as the whole number of the alarms generated in all associated areas.

Figure 9:
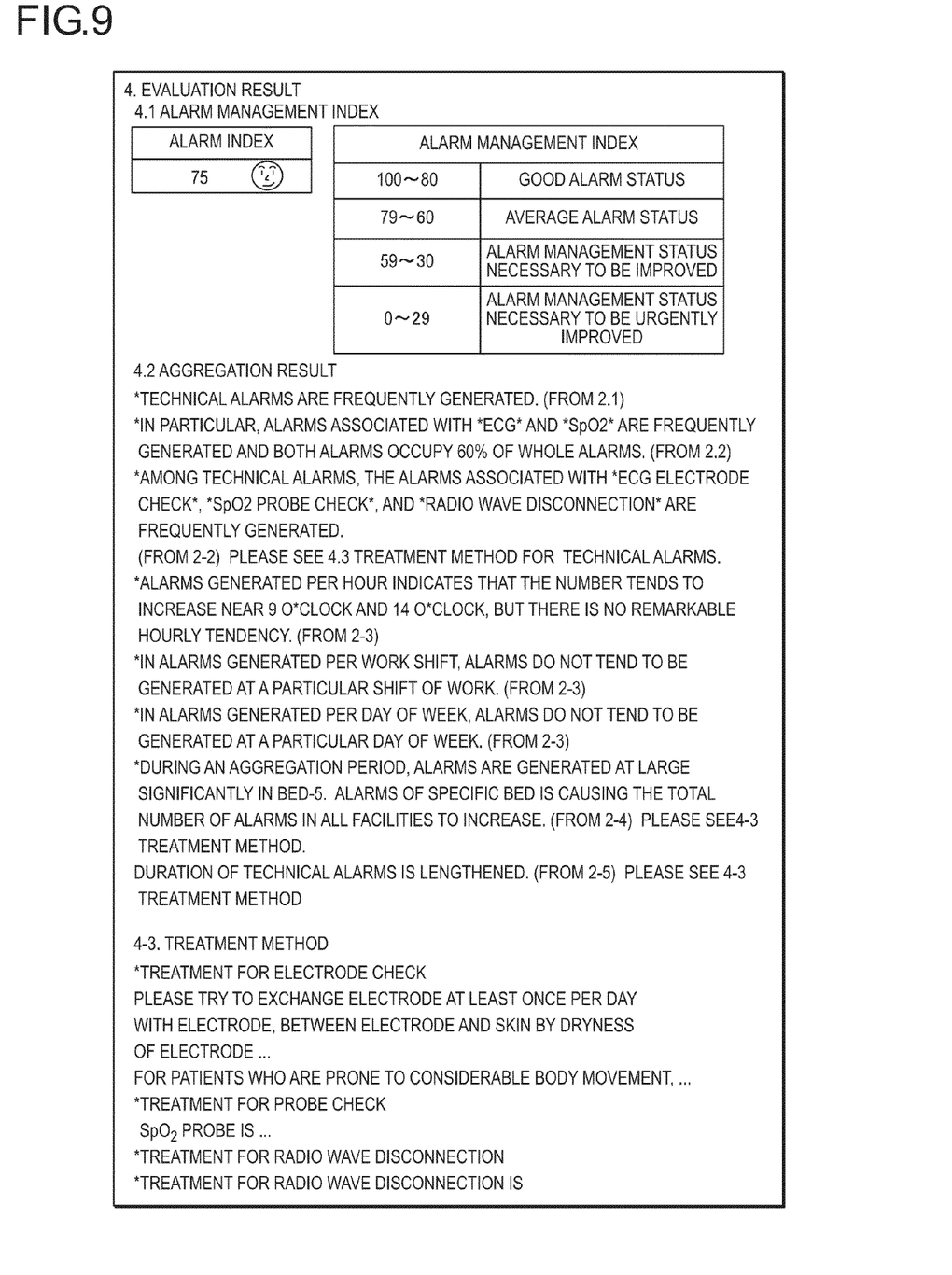
FIG. 9 is a diagram illustrating another example of the evaluation of an alarm generation status according to an embodiment.

FIG. 9 is a diagram illustrating another example of the evaluation of an alarm generation status according to the present embodiment. As illustrated in FIG. 9, evaluation is performed based on the data regarding the numbers of the alarms generated in the above-described manner. Specifically, the alarm index is calculated based on the data and the evaluation is performed based on the alarm index. As the alarm index, for example, the number of the alarms generated at one bed for a day can be used. In calculating the alarm index, a suitable weight may be applied to the vital alarm or the technical alarm. Further, the corresponding suitable evaluation message and the corresponding suitable evaluation mark (a form) are output based on the produced result data. For example, the evaluation message can be displayed for a specific parameter or in association with a day or a time at which the number of the generated alarms is largest. For instance, the alarm generated most frequently and a time and a place in which the number of alarms is largest are evaluated. Also, a treatment method can be output based on the produced resultant data. For example, when the technical alarm for an electrode is numerous, a message that prompts electrode check is output.

As described above, in the present embodiment, the alarm information including the same alarm contents is searched for each of the alarm contents included in the alarm information and stored as a log. And, thus the corresponding alarm information is associated with each other. Then, the numbers of the associated alarms generated are aggregated. In this manner, by associating the alarm information with each other and aggregating the alarm information, a correlation between many alarms generated at different times in the biological information monitoring apparatus can be displayed and output in an easily understandable form. Further, the evaluation and the treatment method are output based on the produced display data. Since the reoccurring pattern, rules, or the like of the alarms can be examined in consideration of the occurrence situations of the previously generated alarms by performing the treatment in accordance with the evaluation and the treatment method, the evaluation and the treatment method can be used as a guideline for improving the future medical treatment. Accordingly, the safer and more comfortable medical treatment can be achieved.

The invention is not limited to the above-described embodiments but may be modified in various forms within the scope of the claims.

An alarm information processing program according to the present embodiment is not limited to the form in which the alarm information processing program is installed in the central monitoring apparatus. The alarm information processing program may be installed in a computer such as a PC and a portable terminal apparatus connected to the network 30 and may be executed by the PC and the portable terminal apparatus. Also, the results of the displayed tables, graphs, evaluations, and the like may be printed by a printer connected through the network or a local connection, or may alternatively be displayed on the biological information monitoring apparatus 10, the central monitoring apparatus 20, or a display unit of the PC or the portable terminal apparatus. Further, the alarm information processing program may be installed in the biological information monitoring apparatus 10. The alarm information may be stored and read based on an alarm generated by the biological information monitoring apparatus itself, by which these alarm contents may be configured to be associated with each other based on the alarm information.

In Step S11, the form in which the alarm information is stored has been described. However, it is not limited thereto. For example, the alarm information may not be stored, but the alarm information may be sequentially read one by one whenever the alarm information is obtained.

In such an embodiment, the tables of the aggregated and summarized results, the evaluation results, and the graphs have hitherto been exemplified. However, the invention is not limited the exemplified forms. Colors, shapes, or the like may be suitably applied to improve recognition.

The units and methods of performing the various processes in the biological information monitoring system according to the present embodiment may be actualized by one of a dedicated hardware circuit and a programmed computer. Such program may be provided by a computer-readable recording medium such as a CD-ROM or a USB memory, or may be provided online through a network such as the Internet. In this case, the program stored in the computer-readable recording medium is generally transmitted and stored in a storage unit such as a hard disk. Alternatively, the program may be provided as single application software or may be embedded as one function of the biological information monitoring system in software of the biological information monitoring system.

What is claimed is:

1. An information processing apparatus comprising:
a reading unit configured to read alarm information from a first plurality of medical apparatuses which generate alarms based on abnormalities of biological information of a plurality of patients or abnormalities of a second plurality of medical apparatuses, wherein the alarm information includes a plurality of alarm information records respectively associated with a plurality of alarms which have been generated, each alarm information record including a first indicator which indicates a type of abnormality that caused the alarm that is associated with the alarm information record; and
a control unit configured to associate alarm information records by identifying all alarm information records which include an identical first indicator.

2. The information processing apparatus as claimed in claim 1, wherein the control unit is configured to associate the alarm information records which include the identical first indicator.

3. The information processing apparatus as claimed in claim 1, further comprising: a display unit configured to display an aggregation result, comprising an aggregation of the alarm information records, as at least one of a numeral, a figure, a table, a graph, a color, and a character.

4. The information processing apparatus as claimed in claim 3, wherein:
each of the alarm information records also include a second indicator indicating a time at which the alarm associated with the alarm information record was generated,
the control unit is configured to associate the alarm information records with alarms generated within a predetermined time period using the second indicator, and
the display unit displays the aggregation result in terms of the predetermined time period.

5. The information processing apparatus as claimed in claim 3, wherein:
the alarm information records each include a third indicator which indicates a type of alarm associated with each alarm information record,
the control unit is configured to associate the alarm information records by identifying all alarm information records which include an identical third indicator, and
the display unit displays the aggregation result in terms of the type of alarm.

6. The information processing apparatus as claimed in claim 3, wherein:
the alarm information records each include a fourth indicator which indicates a location at which the alarm associated with each alarm information record is generated,
the control unit is configured to associate the alarm information records by identifying all alarm information records which include an identical fourth indicator, and
the display unit displays the aggregation result in terms of the location at which the gathered information is generated.

7. The information processing apparatus as claimed in claim 3, wherein the control unit is configured to calculate a duration of time during which the alarm associated with each alarm information record is generated and then stopped, and is configured to associate the alarm information records in terms of the duration of time calculated, and the display unit is configured to display the duration of time calculated.

8. The information processing apparatus as claimed in claim 3, wherein the display unit is further configured to display an evaluation of the aggregated alarm information records.

9. The information processing apparatus as claimed in claim 8 wherein the evaluation of the aggregated alarm information records comprises an output of one of qualitative data and quantitative data.

10. A non-transitory computer readable recording medium stored with an information processing program, said program causing a computer to execute a process comprising
reading alarm information from a first plurality of medical apparatuses which generate alarms based on abnormalities of biological information of a plurality of patients or abnormalities of a second plurality of medical apparatuses, wherein the alarm information includes a plurality of alarm information records respectively associated with a plurality of alarms which have been generated, each alarm information record including a first indicator which indicates a type of abnormality that caused the alarm that is associated with the alarm information record; and associating similar alarm information records by identifying all alarm information records which include an identical first indicator.

* * * * *